United States Patent [19]

Franz

[11] 4,078,065
[45] Mar. 7, 1978

[54] ORGANIC COMPOUNDS

[75] Inventor: Joachim Franz, Riehen, Switzerland

[73] Assignee: Sandoz Ltd., Basel, Switzerland

[21] Appl. No.: 702,157

[22] Filed: Jul. 2, 1976

Related U.S. Application Data

[63] Continuation-in-part of Ser. No. 591,059, Jun. 27, 1975, abandoned.

[30] Foreign Application Priority Data

Jul. 4, 1974 Switzerland ............. 9204/74
Dec. 22, 1975 Switzerland ............ 16588/75

[51] Int. Cl.² ............. A61K 31/48; A61K 31/135
[52] U.S. Cl. ............................. 424/261; 424/330
[58] Field of Search ..................... 424/261, 330

[56] References Cited

PUBLICATIONS

Remington's Pharmaceutical Sciences, (1965), pp. 282–293 and 302–303.
Journal of Pharmaceutical Sciences, vol. 58, No. 10, 1242–1245, (Oct. 1969).

Primary Examiner—Stanley J. Friedman
Attorney, Agent, or Firm—Gerald D. Sharkin; Robert S. Honor; Thomas O. McGovern

[57] ABSTRACT

The present invention relates to a pharmaceutical composition comprising aggregates of diameter of at most 20,000 A, comprising:

component (a) comprising at least one pharmaceutically acceptable active agent, and component (b) comprising at least one pharmaceutically acceptable emulsifier, component (b) having a mean HLB value of 10 to 30 and present in an amount greater than 10 times by weight of component (a).

The composition has enhanced resorption properties.

19 Claims, No Drawings

ORGANIC COMPOUNDS

This is a continuation-in-part of our copending application, Ser. No. 591,059, filed 27th June, 1975 now abandoned.

The present invention relates to a pharmaceutical composition comprising aggregates of diameter of at most 20,000 A, comprising:

component (a) comprising at least one pharmaceutically acceptable active agent, and component (b) comprising at least one pharmaceutically acceptable emulsifer, component (b) having a mean HLB value of 10 to 30 and present in an amount greater than 10 times by weight of component (a).

The present invention also provides a method for increasing the cumulative absorption of a pharmaceutically active agent or agents comprising administering the agent in the form of a composition as defined above.

Component (a) is preferably an active agent which is difficulty absorbable into the bloodstream on enteral, e.g. oral, administration. Such difficulty absorbable active agents are those which are absorbed by the body at a cumulative percentage absorption up to 45% at most, e.g. in amounts below 35% or even below 25% as indicated by standard tests. For example, in one test material is administered p.o. in a ca. 0.008% w/v aqueous solution to the bile fistula rat. The cumulative percentage elimination of material in the bile and in the urine is measured in conventional manner. The dose of material administered is chosen such that the cumulative percentage absorption substantially levels out after 48 hours. In the same test the initial rate of elimination of material in e.g. the bile is also determined in conventional manner.

The present composition exhibits enhanced resorption properties as indicated in standard tests, e.g. by a greater cumulative percentage absorption and initial rate of absorption in the above-indicated test than would be expected for such compositions.

The present compositions are therefore indicated for use with active agents for the treatment of migraine or hypertension or possibly analgesic or antibiotics, when it is desired to obtain high blood level values in the bloodstream as rapidly as possible.

Examples of component (a) include nitrogen-containing compounds, i.e. high molecular, especially heterocyclic compounds, e.g. lysergic acid derivatives, alkaloids such as ergot alkaloids or synthetic or semisynthetic alkaloid derivatives, e.g. ergolene. Preferred examples are e.g. ergotamine or synthetic or semisynthetic lysergic acid derivatives, e.g. hydrogenated derivatives of ergot alkaloids, e.g. dihydroergotoxine, dihydroergocristine and the 13-bromoderivative thereof, dihydroergonine, dihydroergocryptine, dihydroergotamine and the 13-bromo derivative thereof, dihydroergocornine and dihydroergovaline.

Other examples include low molecular weight compounds such as dopamine derivatives such as dopamine double molecule derivatives.

An example of a dopamine derivative is N,N'-(2-methyl-4,5-dihydroxyphenethyl)hexamethylenediamine, or N,N'-Bis[6-(3,4-hydroxyphenyl)ethylamino]hexyl] hexamethylene diamine.

The active agent content may naturally vary considerably and may be adjusted to the desired dose depending on the type of active agents used and the condition to be treated, the amount to be administered per unit dose and the type of composition.

However, in order to obtain a specific therapeutic result, the amount of active agent administered per dose in the composition of the invention may be smaller than the amount of the same active agent in one of the hetherto used formulations required for the obtention of an equal result. In the case of single dosage form, component (a), may amount up to 5% e.g. up to 2.5% by weight in the case of solid preparations and in the case of liquid preparations up to 1% by weight of the composition. For example, component (a) in drop solutions preferably amounts to between 0.05% and 0.6% and in tablets and capsules preferably between 0.2% and 4.0%, especially 0.2 and 2.5%, e.g. from 0.4 to 2.5%.

H.L.B. value (hydrophilic/lipophilic balance) of component (b) is a measure for the relative portion of hydrophilic groups in an emulsifier molecule [see Pharm. Act. Helv. 44, 9 (1969) and H. P. Fiedler, Lexikon der Hilfsstoffe fur Pharmazie, Kosmetik and angrenzende Gebiete, page 263, Edicio Cantor KG. 1971].

It is preferred to use one or more physiologically tolerable emulsifiers having a mean H.L.B. value of 10 to 20, especially 12 to 16. For the production of solid compositions it is preferred to use emulsifiers or emulsifier mixtures which are solid at room temperature. Examples of suitable physiologically tolerable emulsifiers of the group of the non-ionogenic tensides are the tensides of the type of the polyol fatty acid esters of the polyol ethers with higher aliphatic or cyclic alcohols or polyalcohols having emulsifying properties such as polymerization products from ethylene oxide and propylene oxide or propylene glycol. Examples of suitable polyol fatty acid esters are inter alia polyethylene glycol sorbitan fatty acid esters, e.g. polyoxyethylene-4-sorbitan monostearate, such as Tween ® 61 (Atlas Chemical Industries), polyethylene glycol fatty acid esters, e.g. polyoxyethylene-10-stearate such as Myrj ® 52 (Atlas Chemical Industries), polyethylene glycol-400-stearate DAB7, polyoxyethylene glycol glycerin fatty acid esters, e.g. polyoxyethylene castor oil, such as Cremophor ® EL (Bad. Anilin u. Sodafabrik). Examples of suitable polyol ethers of higher alcohols are inter alia polyol ethers of higher fatty alcohols, e.g. polyoxyethylene-20-cetylic ether, such as Brij ® 56 (Atlas Chemical Industries), ethoxylated wool fat alcohols (e.g. with 16 mols of ethylene oxide, such as Solulan ® 16 (American Cholesterol Comp.) or polyols etherified with cholesterin, e.g. cholesterin ethoxylated with approximately 24 mols of ethylene oxide, such as Solulan ® C 24 (American Cholesterol Comp.). Suitable oxyethylenoxy-propylene polymerization products are, for example, polymerization products having a mean molecular weight of approximately 1000 to 10000, e.g. an oxy-ethylenoxy-propylene polymer containing 40% of polyoxyethylene and having a mean molecular weight of approximately 2,900, such as Pluronic ® L 64 (Wyandotte Chemicals), an oxy-ethylenoxy-propylene polymer having a mean molecular weight of approximately 3,500, such as Pluronic ® P 65 (Wyandotte Chemicals) or an oxy-ethylenoxy-propylene polymer containing 80% of polyoxyethylene and having a mean molecular weight of approximately 8,700, such as Pluronic ® F 68 (Wyandotte Chemicals). The alkyl groups in the dialkylsulpho-succinates may contain from 4 to 10 carbon atoms. A suitable salt is an alkali metal salt, e.g. sodium. A preferred example of a dialkyl-sulphosuccinate is sodium dioctyl sulphosuccinate, such as Aerosol ® OT (American Cyanamid Co.).

It may be convenient to use different types of emulsifiers depending on the chemical and physical properties, molecule size and form of the component (a) used and component (c), mentioned hereafter.

When ergot alkaloids or synthetic or semisynthetic lysergic acid derivatives are used, then it is particularly convenient to use polyols etherified with cholesterin, e.g. cholesterin ethoxylated with about 24 mols of ethylene oxide.

It is also convenient to use oxy-ethylenoxypropylene polymers, e.g. Pluronic ® L 64 or Pluronic ® P 65 or emulsifier mixtures containing oxy-ethylenoxy-propylene polymers.

Also suitable are polyethylene glycol fatty acid esters, e.g. polyoxyethylene-40-stearate or polyethylene glycol-400-stearate DAB7.

The amounts of emulsifier to be used may vary depending on the emulsifier used, especially its chemical and physical properties, the type and amount of adjuvants used, the type of active agents used and the desired extent of improvement in resorption. The upper limit of movement of emulsifier to be used will naturally depend on the physiological tolerability of said emulsifier, taking into consideration the planned duration of treatment and frequency of administration. The components in the composition are preferably present in such amounts that the total amount of component (b) does not exceed 50 mg/unit dose. The ratio of total amount of component (b) to component (a) may, for example, be from 10:1 to 50:1, preferably 20:1 to 30:1. In anhydrous administration forms, the total quantity of emulsifer may amount up to 60%, e.g. in unit-dose preparations preferably between 20% and 50%. In water-containing compositions, the concentration of component (b) conveniently is between the critical micelle concentration (CMC) and maximal addition concentration (MAC) of the emulsifiers used. The total amount of component (b) in water-containing administration forms preferably is between 1% and 5%.

The aggregates may conveniently contain as component (c) a further pharmaceutical carrier, preferably a lipoid carrier. Component (c) is preferably present in an amount 25 times or especially up to 10 times the amount of component (a) present.

Lipoid carrier materials which may be used are, for example, monovalent or polyvalent lower alcohols partially or completely esterified with higher aliphatic carboxylic acids, preferably alcohols of 2-3 carbon atoms, especially glycerin or propylene glycol, or condensates thereof, e.g. polyglycerins. For the production of solid compositions it is convenient to use lipoid carrier materials which are solid at room temperature, and for the production of liquid mechanical preparations liquid lipoid carrier materials or mixtures of solid and/or liquid lipoid carrier materials which are liquid at room temperature. Especially suitable solid lipoid carrier materials are only partially esterified alcohols, especially saturated monoglycerides and diglycerides. The aliphatic carboxylic acids contained in the solid esters may preferably contain 12 to 20 carbon atoms and may be straight chain or branched and/or hydroxylated. Especially suited for the production of liquid medicinal preparations are completely esterified alcohols, especially triglycerides, e.g. esters of unsaturated carboxylic acids or saturated carboxylic acids, preferably containing 8 to about 12 carbon atoms. Examples of suitable esters are inter alia monoglycerides, diglycerides or triglycerides of saturated or unsaturated fatty acids, e.g. glycerin monolaurate, monomyristate, monooleate or monoricinoleate, peanut oil, oily triglyceride mixtures of saturated vegetable fatty acids containing 8 to 12 carbon atoms or propylene glycol esters, e.g. propylene glycol monostearate.

The non-aggregate portion of the composition may contain further pharmaceutical carriers or diluents [component (d)] which do not hinder the formation of the active agent- and emulsifier-containing aggregates or impair the stability of the resulting aggregates.

For example, it is convenient to add water-soluble solid or liquid physiologically tolerable monovalent or polyvalent alcohols. Examples of suitable alcohols are: ethanol, propylene glycol, glycerin, sugar aocohols and polyethylene glycols having a mean molecular weight of, for example, 300 to 10,000. An addition of polyalcohols, e.g. polyethylene glycol, which will promote the solubilization of the active agents which are difficultly soluble in water, is particularly desirable when the emulsifier mixture used contains no oxyethylenoxy-propylene polymers or only small amounts thereof. For the production of liquid administration forms it is preferred to add liquid alcohols, e.g. lower monovalent or polyvalent alcohols and/or polyethylene glycols with mean molecular weights below 2,000, preferably between 300 and 1,500. For solid medicinal preparations it is convenient to use alcohols which are solid at room temperature, e.g. sugar alcohols and/or polyethylene glycols having mean molecular weights over 1,800, preferably between 2,000 and 10,000, especially 5,000-7,000.

The portion of the composition comprising polyalcohols and emulsifiers may be composed of one or several non-emulsifying polyalcohols, preferably polyethylene glycols, and one or several non-ionic tensides of the polyol fatty acid ester type, preferably polyoxyethylene-sorbitan fatty acid esters, and/or of the ethoxylated higher alcohol type, preferably ethoxylated chlolesterin, and/or dialkylsulphosuccinates, or may consist of polyalcohols having emulsifying properties, such as polyoxyethylene-polyoxypropylene polymers, optionally in admixture with one or several of the tensides mentioned above and/or non-emulsifying polyalcohols. Especially suitable is a combination of ethoxylated cholesterin and polyethylene glycols and/or polyoxyethylene-polyoxypropylene polymers.

Water-containing compositions of the invention may contain between 20% and 95 e.g. up to 90%, preferably between 30% and 70%, e.g. between 30 and 50% by weight of water and optionally further adjuvants. The alcohol or polyol content of the aqueous liquid may, for example, be between 0% and 50%, preferably between 20% and 40% by weight of the formulation.

Anhydrous liquid preparations may contain the active agent-and emulsifier-containing aggregates finely distributed in a water-soluble and/or water-dispersible liquid carrier material consisting of one or several liquid carriers and optionally further adjuvants. Suitable liquid carrier materials are especially physiologically tolerable lower monovalent or polyvalent alcohols and/or liquid polyethylene glycols, 2,000. polyethylene glycols having mean molecular weights below 2000.

Liquid compositions may contain as further components additional pharmaceutical adjuvants, e.g. preserving and flavouring agents and buffer materials. The liquid preparations may contain further physiologically tolerable water-soluble and/or water-dispersible solid materials, especially when they are to be worked up into solid dosage forms.

The solid medicinal preparations of the invention contain the active agent and emulsifier-containing aggregates finely distributed in a carrier material which is formed from one or several water-soluble and/or water-dispersible solid materials and optionally further pharmaceutical adjuvants.

Suitable physiologically tolerable, water-soluble solid materials are, for example, polyethylene glycols which are solid at room temperature, preferably polyethylene glycols having a mean molecular weight between about 2,000 and 10,000, preferably between 6,000 and 10,000, polyvinyl pyrrolidones, excess solid oxyethylenoxypropylene polymers, sugars, e.g. lactose, sugar alcohols, e.g. mannitol or sorbitol, and carboxymethyl cellulose.

The solid materials dispersible in water are preferably used in the form of finely dispersed powders which owing to their large surface are capable of absorbing the finely distributed active agent- and emulsifier-containing aggregates. Suitable solid materials are, for example, physiologically tolerable, in water dispersible, non-swelling inorganic and/or organic carrier materials, insofar as they do not irreversibly bind the active agents used. Suitable inorganic carrier materials are, for example, dicalcium phosphates or highly dispersed silicic acids having a tapped volume preferably between 250 and 1,000 cc/100 g, especially wet precipitated silicic acid.

Depending on the desired formulation, the solid medicinal preparations may contain as further components additional physiologically tolerable pharmaceutical adjuvants, e.g. preserving and flavouring agents and any desired tabletting adjuvants generally used in the production of tablets or any desired suppository masses used in the production of suppositories.

The active agent-containing aggregates present may have a diameter up to 20,000 A, preferably between 100 and 10,000 A, especially below 2,000 A. or above 400 A.

In aqueous medicinal preparations the distribution of the emulsifer- and active agent-containing aggregates in the aqueous liquid preferably is so fine that transparent or slightly opalescent liquids are obtained. The diameter of the active agent- and emulsifier-containing aggregates preferably is less than 2,000, especially less than 1,000 A.

The anhydrous solid or liquid compositions of the invention are dried preparations or liquid preparations which contain the active agent-containing aggregates preferably so finely distributed that when brought into an aqueous medium they rapidly give a transparent or slightly opalescent liquid, wherein the difficultly absorbable active agent or agents are solubilized in the form of finely distributed active agent- and emulsifier-containing aggregates.

The new compositions of the invention may be liquid or solid and are preferably administered orally. The liquid compositions of the invention may, for example, be administered as a drop solution or syrup. Anhydrous liquid compositions may also be filled into soft gelatin capsules for the production of unit-dose administration forms. The preferred water-containing compositions are drop solutions. Suitable solid administration forms are, for example, powders, granulates, capsules, tablets or film tablets for oral administration, or suppositories for rectal administration.

A preferred form of the compositions of the invention are liquid or preferably solid galenic preparations of ergot alkaloids or synthetic or semisynthetic lysergic acid derivatives, wherein the total amount of polyalcohols and emulsifiers in the case of water-containing preparations preferably is between 15% and 80 e.g. up to 70% of the total formulation and in the case of anhydrous preparations between 40% and 99% of the total formulation.

The compositions may be obtained by a process including the step of formulating aggregates having at most a diameter of 20,000 A of components (a) and (b) as defined above.

The production of the liquid compositions may be effected in accordance with the invention by dispersing components (a) and (b) if desired with the addition of further pharmaceutical adjuvants, in the liquid carrier material, e.g. in an anhydrous medium or in water or in a water-containing medium, preferably using ultrasonic waves and/or high speed stirrers.

In accordance with an embodiment of the process the active agents may first be dissolved with slight heating in the tensides, optionally with the addition of lipoid carrier materials, this mixture may subsequently be diluted with the liquid carrier materials and homogenized while treating with ultrasonic wave or high-speed stirrers.

The production of the solid compositions may also be effected in accordance with the invention by carefully removing the liquid carrier materials, e.g. water and/or lower alcohols, from primarily produced liquid preparations and converting the resulting powdery or spongy-porous dry preparation in known manner into the desired administration form.

The careful drying of the liquid preparations may be effected in known manner, e.g. by freeze-drying or spray-drying. For example, the liquid preparations may be freezed at temperatures between $-80°$ and $-50°$ C and then lyophilized in a high vacuum, or the liquid preparations may be atomized in a drying chamber and dried by a warm air stream, e.g. at temperatures from 120° to 180° C.

If desired, the resulting dry preparations may subsequently be worked up in known manner, optionally with the addition of further suitable pharmaceutical adjuvants such as tabletting adjuvants and suppository mass, e.g. filled into capsules, granulated, tabletted or moulded into suppositories.

In the following non-limitative Examples all temperatures are indicated in degrees Centigrade.

Polytron is a trade mark.

EXAMPLES 1 - 30

Water-containing drop solutions of difficultly absorbable active agents

The formulations of Examples 1 - 28 having the composition indicated in the following Table 1, are produced as follows:

The difficultly absorbable active agents are dissolved with slight heating (at temperatures between 30 and 50°) in the emulsifiers and any lipoid carrier materials which may present, optionally with the addition of part of the polyalcohols.

The water or an aqueous solution of any further adjuvants or a mixture of water and any polyalcohols used is added to the above solution while stirring vigorously with a polytron homogenizer, and the resulting mixture is homogenized for 5 to 6 minutes by treatment with ultrasonic wave and/or a polytron homogenizer.

The resulting homogeneous liquids are filled into bottles fitted with droppers.

| | | |
|---|---|---|
| a) Solulan C 24 ® | of | American Cholesterol Comp. |
| b) Pluronic L 64 ® | " | Wyandotte Chemicals |
| c) " P 65 ® | " | " |
| d) " F 68 ® | " | " |
| e) Tween 61 ® | " | Atlas Chemical Industries |
| f) Myrj 52 ® | " | " |
| g) Brij 56 ® | " | " |
| h) Cremophor HL ® | " | Badische Anilin- und Sodafabrik |
| i) Cremophor AP ® | " | " |
| j) Miglyol 812φ | " | Henkel |
| k) Tegemuls 70 ® | " | Goldschmidt AG |
| l) Tween 65 ® | " | Atlas Chemical Industries |
| m) Aerosol OT ® | " | American Cyanamid Co. |

Table 1

| | Water-containing drop solutions | | | | | | | |
|---|---|---|---|---|---|---|---|---|
| Example No. | 1 | 2 | 3 | 4 | 5 | 6 | 7 | 8 |
| mg of active agents: | | | | | | | | |
| Dihydroergocristine | 360 | 400 | 400 | | 800 | 800 | 800 | 800 |
| Dihydroergovaline | | | | 400 | | | | |
| Dihydroergotoxine | | | | | | | | |
| Dihydroergocornine | | | | | | | | |
| Dihydroergocryptine | | | | | | | | |
| Ergotamine | | | | | | | | |
| 13-bromo-dihydroergotamine | | | | | | | | |
| 13-bromo-dihydroergocryptine | | | | | | | | |
| N,N-(2-methyl-4,5-dihydroxyphenethyl)-hexamethylenediamine | | | | | | | | |
| g of emulsifiers: | | | | | | | | |
| Cholesterin ethoxylated with approx. 24 mols of ethylene oxide $^{a)}$ | 2.5 | | 2.0 | | 2.0 | | 3.0 | |
| Oxy-ethylenoxy-propylene polymer, mean molecular weight 2900 $^{b)}$ | 6.0 | 6.0 | | 1.5 | 13 | 12 | | |
| Oxy-ethylenoxy-propylene polymer, mean molecular weight 3500 $^{c)}$ | | | | | | | | |
| Oxy-ethylenoxy-propylene polymer, mean molecular weight 8700 $^{d)}$ | | | 2.0 | | | | | 8 |
| Polyoxyethylene-4-sorbitan monostearate $^{e)}$ | | 2.5 | | | | 5 | | |
| Polyoxyethylene-40-stearate $^{f)}$ | | | | 2.5 | | | 5 | |
| Polyoxyethylene-10-cetylic ether $^{g)}$ | | | | | | | | |
| Polyoxyethylene castor oil $^{h)}$ | | | | | | | | |
| Polyethylene glycol-400-stearate DAB7 $^{i)}$ | | | | | | | | |
| Polyethylene-20-sorbitan tristearate $^{l)}$ | | | | | | | | |
| Sodium dioctyl sulphosuccinate $^{m)}$ | | | | | | | | |
| g of lipoid carrier materials: | | | | | | | | |
| Liquid triglyceride of saturated fatty acids of 8–12 carbon atoms $^{j)}$ | 0.9 | | | 1.8 | 1.8 | 3.5 | 3.5 | |
| Glycerin monolaurate | | | 2.0 | | | | | 8 |
| Glycerin monostearate palmitate $^{k)}$ | | | | | | | | |
| Glycerin monoricinoleate | | | | | | | | |
| Glycerin monooleate | | | | | | | | |
| Propylene glycol monostearate | | | | | | | | |
| Glycerin monomyristate | | | | | | | | |
| Glycerin monoisostearate | | | | | | | | |
| g of polyalcohols: | | | | | | | | |
| Polyethylene glycol 300 | 20 | 20 | | | 40 | 40 | | |
| Polyethylene glycol 400 | | | | | | | | |
| Polyethylene glycol 600 | | | 16 | | | | | |
| Polyethylene glycol 1500 | | | 10 | 18 | | | 40 | |
| Polyethylene glycol 2000 | | | | | | | | |
| Glycerin | | | | | | | | |
| g of further adjuvants: | | | | | | | | |
| Water | 20 | 20 | 15 | 27+ | 29.5 | 38.7 | 50.7 | 82.2 |

| Example No. | 9 | 10 | 11 | 12 | 13 | 14 | 15 | 16 |
|---|---|---|---|---|---|---|---|---|
| mg of active agents: | | | | | | | | |
| Dihydroergocristine | 800 | | | | | | | |
| Dihydroergovaline | | 800 | 800 | 800 | | | | |
| Dihydroergotoxine | | | | | 400 | 400 | | |
| Dihydroergocornine | | | | | | | 800 | |
| Dihydroergocryptine | | | | | | | | 600 |
| Ergotamine | | | | | | | | |
| 13-bromo-dihydroergotamine | | | | | | | | |
| 13-bromo-dihydroergocryptine | | | | | | | | |
| N,N-(2-methyl-4,5-dihydroxyphenethyl)-hexamethylenediamine | | | | | | | | |
| g of emulsifiers: | | | | | | | | |
| Cholesterin ethoxylated with approx. 24 mols of ethylene oxide $^{a)}$ | 3 | | | | | | 3 | |
| Oxy-ethylenoxy-propylene polymer, mean molecular weight 2900 $^{b)}$ | | 10 | 10 | 10 | 12 | 6 | | 10 |
| Oxy-ethylenoxy-propylene polymer, mean molecular weight 3500 $^{c)}$ | | | | | | 6 | | |
| Oxy-ethylenoxy-propylene polymer, mean molecular weight 8700 $^{d)}$ | 5 | | | | | | | |
| Polyoxyethylene-4-sorbitan monostearate $^{e)}$ | | | | | | | | |
| Polyoxyethylene-40-stearate $^{f)}$ | | | | | | | 5 | |
| Polyoxyethylene-10-cetylic ether $^{g)}$ | | | | | | | | |
| Polyoxyethylene castor oil $^{h)}$ | | | 10 | | | | | 5 |
| Polyethylene glycol-400-stearate DAB7 $^{i)}$ | | | | | 5 | | | |
| Polyethylene-20-sorbitan tristearate $^{l)}$ | | 10 | | | | | | |

Table 1-continued

Water-containing drop solutions

| | | | | | | | |
|---|---|---|---|---|---|---|---|
| Sodium dioctyl sulphosuccinate [m] | | | | | | | |
| g of lipoid carrier materials: | | | | | | | |
| Liquid triglyceride of saturated fatty acids of 8–12 carbon atoms [j] | | | | | 1.0 | | 1.5 |
| Glycerin monolaurate | 5 | | | | | | |
| Glycerin monostearate palmitate [k] | | | | | | | |
| Glycerin monoricinoleate | | | | | | | |
| Glycerin monooleate | | | | | | | |
| Propylene glycol monostearate | | | | | | | |
| Glycerin monoisostearate | | | | | | | |
| g of polyalcohols: | | | | | | | |
| Polyethylene glycol 300 | | 40 | 40 | 45 | 40 | 40 | |
| Polyethylene glycol 400 | | | | | | | 40 |
| Polyethylene glycol 600 | 5.5 | | | | | | |
| Polyethylene glycol 1500 | | | | | | 40 | |
| Polyethylene glycol 2000 | | | | | | | |
| Glycerin | | | | | 28 | | |
| g of further adjuvants: | | | | | | | |
| Water | 34.2 | 39.2+ | 39.2 | 44.2+ | 71.6 | 19.5 | 54.2 | 42.9 |

| Example No. | 17 | 18 | 19 | 20 | 21 | 22 | 23 | 24 |
|---|---|---|---|---|---|---|---|---|
| mg of active agents: | | | | | | | | |
| Dihydroergocristine | | 400 | 400 | 400 | 200 | 200 | 800 | 200 |
| Dihydroergovaline | | | | | | | | |
| Dihydroergotoxine | | | | | | | | |
| Dihydroergocornine | | | | | | | | |
| Dihydroergocryptine | | | | | | | | |
| Ergotamine | 800 | | | | | | | |
| 13-bromo-dihydroergotamine | | | | | | | | |
| 13-bromo-dihydroergocryptine | | | | | | | | |
| N,N-(2-methyl-4,5-dihydroxyphenethyl)-hexamethylenediamine | | | | | | | | |
| g of emulsifiers: | | | | | | | | |
| Cholesterin ethoxylated with approx. 24 mols of ethylene oxide [a] | | 10 | 6 | 6 | 3 | 3 | 8 | 2.5 |
| Oxy-ethylenoxy-propylene polymer, mean molecular weight 2900 [b] | | | | | | | | |
| Oxy-ethylenoxy-propylene polymer, mean molecular weight 3500 [c] | 8 | | | | | | | |
| Oxy-ethylenoxy-propylene polymer, mean molecular weight 8700 [d] | | | | | | | | |
| Polyoxyethylene-4-sorbitan monostearate [e] | | | | | | | | |
| Polyoxyethylene-40-stearate [f] | | | | | | | | |
| Polyoxyethylene-10-cetylicether [g] | | | | | | | | |
| Polyoxyethylene castor oil [h] | | | | | | | | |
| Polyethylene glycol-400-stearate DAB7 [i] | | | | | | | | |
| Polyethylene-20-sorbitan tristearate [l] | | | | | | | | |
| Sodium dioctyl sulphosuccinate [m] | | | | | | | | |
| g of lipoid carrier materials: | | | | | | | | |
| Liquid triglyceride of saturated fatty acids of 8–12 carbon atoms [j] | | | | | | | | |
| Glycerin monolaurate | | | 2 | | | | | |
| Glycerin monostearate palmitate [k] | | | | | | | | |
| Glycerin monoricinoleate | | | | 2 | | | | |
| Glycerin monooleate | | | | | 1 | | | |
| Propylene glycol monostearate | | | | | | 1 | | |
| Glycerin monomyristate | | | | | | | 1 | |
| Glycerin monoisostearate | | | | | | | | 0.5 |
| g of polyalcohols: | | | | | | | | |
| Polyethylene glycol 300 | | | | | | | | |
| Polyethylene glycol 400 | | | | | | | | |
| Polyethylene glycol 600 | | | | | | | 40 | |
| Polyethylene glycol 1500 | | | | | | | | |
| Polyethylene glycol 2000 | 10 | | | | | | | |
| Glycerin | | | | | | | | |
| g of further adjuvants: | | | | | | | | |
| Water | 31.2 | 89.6 | 91.6 | 91.6 | 95.8 | 95.8 | 53.2 | 96.8 |

| Example No. | 25 | 26 | 27 | 28 | 29 | 30 |
|---|---|---|---|---|---|---|
| mg of active agents: | | | | | | |
| Dihydroergocristine | 800 | | | | | |
| Dihydroergonine | | | | | 600 | |
| Dihydroergotamine | | | | | | 300 |
| Dihydroergocornine | | | | | | |
| Dihydroergocryptine | | | | | | |
| Ergotamine | | | | | | |
| 13-bromo-dihydroergotamine | | 120 | | | | |
| 13-bromo-dihydroergocryptine | | | 50 | | | |
| N,N-(2-methyl-4,5-dihydroxyphenethyl)-hexamethylenediamine | | | | 80 | | |
| g of emulsifiers: | | | | | | |
| Cholesterin ethoxylated with approx. 24 mols of ethylene oxide [a] | 3 | 5.8 | | 5 | 6 | 3 |
| Oxy-ethylenoxy-propylene polymer, mean molecular weight 2900 [b] | | | 2.25 | | | |
| Oxy-ethylenoxy-propylene polymer, mean molecular weight 3500 [c] | | | | | | |
| Oxy-ethylenoxy-propylene polymer, mean molecular weight 8700 [d] | | | | | | 1 |

Table 1-continued

| Water-containing drop solutions | | | | | | |
|---|---|---|---|---|---|---|
| Polyoxyethylene-4-sorbitan monostearate [e)] | | | | | | |
| Polyoxyethylene-40-stearate [f)] | | | | | | |
| Polyoxyethylene-10-cetylic ether [g)] | | | | | | |
| Polyoxyethylene castor oil [h)] | | | | | | |
| Polyethylene glycol-400-stearate DAB7 [i)] | | | | | | |
| Polyethylene-20-sorbitan tristearate [j)] | | | | | | |
| Sodium dioctyl sulphosuccinate [m)] | 5 | | | | | |
| g of lipoid carrier materials: | | | | | | |
| Liquid triglyceride of saturated fatty acids of 8–12 carbon atoms [j)] | 3.5 | | | | | |
| Glycerin monolaurate | | | 1 | | | |
| Glycerin monostearate palmitate [k)] | | | | | | |
| Glycerin monoricinoleate | | | | | | |
| Glycerin monooleate | | | | | | |
| Propylene glycol monostearate | | | | | | |
| Glycerin monomyristate | | | | | | |
| Glycerin monoisostearate | | | | | | |
| g of polyalcohols: | | | | | | |
| Polyethylene glycol 300 | 45 | 47 | | | | 25 |
| Polyethylene glycol 400 | | | 3 | | 30 | |
| Polyethylene glycol 600 | | | | | | |
| Polyethylene glycol 1500 | | | | | | |
| Polyethylene glycol 2000 | | | | | | |
| Glycerin | | | | | | |
| g of further adjuvants: | | | | | | |
| Water | 46 | 47+ | 3+ | 40+ | 50+ | 40+ |

+Buffered to pH value 4.3 with a buffer mixture of sodium acetate/acetic acid.

EXAMPLE 31:

Dihydroergotamine-containing drop solution 60 mg of dihydroergotamine mesylate are added together with 1.5 g of cholesterin ethoxylated with approx. 24 mols of ethylene oxide [a)] to 60 cc of water adjusted to pH 4.1 with a buffer mixture of sodium acetate/acetic acid, and homogenized with a polytron homogenizer. The clear liquid is filled into bottles fitted with droppers.

EXAMPLE 32:

Dihydroergotamine-containing anhydrous drop solutions a. 2 g of dihydroergotamine are added together with 50 g of cholesterin ethoxylated with approx. 24 mols of ethylene oxide [a)] to 500 g of polyethylene glycol 400 while heating to 50° in a water bath, treatment is effected with ultra sonic waves for 5 minutes, and the resulting clear liquid is filled into bottles fitted with droppers.

b. The process is effected as described in section a) above, except that a mixture of 250 g of polyethylene glycol 400 and 250 g of glycerin is used in place of 50 g of polyethylene glycol 400.

EXAMPLE 33:

Dihydroergonine-containing soft gelatin capsules 3 g of dihydroergonine are added together with 75 g of cholesterin ethoxylated with approx. 24 mols of ethylene oxide [a)] to 150 cc of polyethylene glycol 300 while heating in a water bath of 50° and subjecting to ultrasonic waves. The clear liquid is subsequently filled into soft gelatin capsules in quantities of 100 mg/capsule.

EXAMPLE 34:

Dihydroergocristine-containing capsules 300 mg of dihydroergocristine are dissolved together with 1.7 g of cholesterin ethoxylated with approx. 24 mols of ethylene oxide [a)] and 1.2 g of glycerin monolaurate while heating to 40°, and homogenized with the addition of 30 g of a 22% solution of oxy-ethylenoxy-propylene polymers having a mean molecular weight of 8700 [d)] in water. After diluting with 50 cc of water, freezing is rapidly effected in a rotating flask at −80° and lyophilization is effected in a high vacuum. As lyophilization progresses the dry material is gradually heated to 25° – 30°. The resulting dry preparation is subsequently filled into capsules in quantities of 50 mg/capsule.

EXAMPLE 35:

Dihydroergotamine-containing capsules 30 mg of dihydroergotamine are dissolved together with 750 mg of cholesterin ethoxylated with approx. 24 mols of ethylene oxide [a)] in 50 cc of absolute ethanol, and the solution is evaporated to dryness in a vacuum at 30°. The residue is homogenized with a polytron homogenizer for about 5 minutes while gradually adding 100 cc of distilled water. 225 mg of highly dispersed silicic acid [n)] are suspended in the resulting clear liquid, and the suspension is homogenized by treatment with ultrasonic waves at 30° for 3 minutes. The suspension is freezed at −80° and subsequently lyophilized. The lyopholized product is filled into gelatin capsules in quantities of 100 mg/capsule.

EXAMPLE 36:

Dihydroergovaline-containing lyophilized product in freeze-dried ampoules 400 mg of dihydroergovaline are dissolved together with 10 g of cholesterin ethoxylated with approx. 24 mols of ethylene oxide [a)] and 40 g of polyethylene glycol 2000 in 300 cc of absolute ethanol. The solution is evaporated to dryness in a rotary evaporator at 30°. 200 cc of distilled water are slowly added to the residue while homogenized continually with the polytron homogenizer. The clear micellar solution of the active agent is filled into ampoules (2 mg of dihydroergovaline per ampoule) and the ampoules are rapidly freezed at −80°, lyophilized and sealed in a vacuum.

The dry preparations having the composition indicated in Table 2 may also be produced in a manner analogous to that described in Examples 34 – 36, and filled into capsules or dry ampoules or granulated and- /or tabletted with the addition of suitable galenic adjuvants:

n. Silicic acid K320 (tapped volume about 500 cc/100 g) of the firm Degussa o. Solulan C16 ® of the firm American Cholesterol Comp. p. PVP K30 ® of the firm Badische Anilin- und Sodafabrik g. Primojel ® of the firm Scholten's Chemische Fabrieken N.V.

-continued

| Components | Example A | Example B |
|---|---|---|
| mg conc. acetic acid Ph.Helv.V | 4.2 | 7.0 |
| mg ethanol 94% w/w | 150 | 150 |

Table 2

| Example No. | 37 | 38 | 39 | 40 | 41 | 42 | 43 | 44 | 45 | 46 | 47 | 48 | 49 |
|---|---|---|---|---|---|---|---|---|---|---|---|---|---|
| g of active agents: | | | | | | | | | | | | | |
| Dihydroergovaline | 0.8 | 0.4 | | | | | | | | | | | |
| Dihydroergotamine | | | 3 | 2 | 3 | 2 | 2 | 3 | 3 | 3 | 3 | 3 | 3 |
| g of emulsifiers: | | | | | | | | | | | | | |
| Oxy-ethylenoxy-propylene polymer, mean molecular weight 8700 $^{d)}$ | | | | | | | | | | | | | 20 |
| Cholesterin ethoxylated with approx. 24 mols of ethylene oxide $^{e)}$ | 20 | 10 | 75 | 42 | 75 | 25 | 25 | 60 | 60 | 75 | 35 | 45 | 20 |
| Cholesterin ethoxylated with approx. 16 mols of ethylene oxide $^{o)}$ | | | | | | 15 | | | | | | | |
| Polyoxyethylene-10-cetylic ether $^{g)}$ | | | | | | | 10 | | | | | | |
| g of lipoid carrier materials: | | | | | | | | | | | | | |
| Glycerin monomyristate | | | | | | | | | | | 1 | | |
| Glycerin monolaurate | | | | | | | | | | | | 2 | |
| g of polyalcohols: | | | | | | | | | | | | | |
| Polyethylene glycol 2000 | 78.2 | | | | 40 | | | | 90 | | | | |
| Polyethylene glycol 6000 | | 20 | | | | | | | | | | | |
| Polyethylene glycol 10000 | | | | | 10 | | | | | | | | |
| g of further adjuvants: | | | | | | | | | | | | | |
| Dispersed silicic acid $^{n)}$ | 20 | | 22 | 56 | | | 20 | | | | 20 | 10 | 20 |
| Dicalcium phosphate | | | | | 300 | | | | | | | | |
| Mannitol | | | | | | | | 20 | | | | 10 | 10 |
| Polyvinyl pyrrolidone, mean molecular weight 40000 $^{p)}$ | | | | | | | | | 10 | | | | |
| Lactose | | | | | | | | | | 50 | | | |
| Carboxymethyl cellulose $^{q)}$ | | | | | | | | | | 300 | | | |

EXAMPLE 50:

Water-containing drop solutions of dihydroergotoxin

The formulations of Examples A and B, having the compositions indicated in the following table, are produced as follows.

The ingredients are dissolved, with gentle heating if necessary, in ethanol and made up to the desired volume with liquid carrier materials and water. The resulting solution is then decanted, if desired under carbon dioxide, into tightly sealable glass bottles.

| Components | Example A | Example B |
|---|---|---|
| mg dihydroergotoxin methane sulphate | 1.0 | 1.0 |
| mg Nipakombin ®* | 0.8 | 0.8 |
| mg sodium acetate Ph.Helv.V | 1.68 | 1.7 |
| mg cholesterin ethoxylated with approx. 24 mols of ethylene oxide $^{a)}$ | 25 | 25 |
| mg glycerine | — | 400 |
| demineralised water | to 1.0 ml | to 1.0 ml |

*mixture of p-hydroxy-benzoic acid methyl ester and p-hydroxy-benzoic acid propylester (2:1)

EXAMPLE 51:

Water-free drop solution of dihydroergotoxin

The formulations of Examples A to G, having the compositions indicated in the following table, are produced as follows.

The solid ingredients are dissolved, with gentle heating if necessary, in the liquid carrier materials and made up to the desired volume. The resulting solution is then decanted, if desired under carbon dioxide, into tightly sealable glass bottles.

| Component | A | B | C | D | E | F | G |
|---|---|---|---|---|---|---|---|
| mg dihydroergotoxin methane sulphonate | 1.0 | 1.0 | 1.0 | 1.0 | 1.0 | 1.0 | — |
| mg dihydroergotoxin | — | — | — | — | — | — | 1.0 |
| mg cholesterin ethoxylated with approx. 24 mols of ethylene oxide $^{a)}$ | 25 | 25 | 25 | 25 | 25 | 25 | 25 |
| mg sodium benzoic acid sulphimide* | 0.5 | 0.5 | 0.5 | 0.5 | — | — | — |
| mg dibutyl phthalate | — | — | — | — | — | — | 500 |
| mg absolute ethanol | 400 | 400 | 400 | 400 | 400 | 400 | — |
| tetraglycol** | — | to 1 ml | — | — | — | — | — |
| 4-hydroxymethyl-2,2-dimethyl-1,3-dioxolane + | — | — | to 1 ml | — | — | — | 500 |
| 2-methyl-2,4-pentadiol*** | to 1 ml | — | — | — | to 1 ml | — | — |
| glycerinformal++ | — | — | — | to | — | to | — |

-continued

| Component | Example | | | | | | |
|---|---|---|---|---|---|---|---|
| | A | B | C | D | E | F | G |
| | | | | 1 ml | | 1 ml | |

LEGEND
*Saccharin-sodium Ph.Helv.VI. Hoechst AG, Frankfurt
**Polyethyleneglycol ether of tetrahydrofurfuryl alcohol (containing ca. 2 mol of ethylene oxide/mol). Welding and Co., Hamburg
***Hexylene glycol. Distillers Co., London
++A mixture of 4-hydroxymethyl-1,3-dioxolane and 5-hydroxy-1,3-dioxane prepared from glycerine and formaldehyde. Oesterreichische Stickstoffwerke AG. Linz.
+Solketal®. Chemomedica, Vienna.

EXAMPLE 52:

Oily water-free drop solutions of dihydroergotoxin

The formulations of Examples A to F, having the compositions indicated in the following table, are produced as follows.

The ingredients are dissolved, with gentle heating if necessary, in ethanol and made up to the desired volume with liquid carrier materials. The resulting solution is then decanted, if desired under nitrogen, into tightly sealable glass bottles.

| Component | Example | | | | | |
|---|---|---|---|---|---|---|
| | A | B | C | D | E | F |
| mg dihydroergotoxin methane sulphonate | 1.0 | 1.0 | 1.0 | 1.0 | 1.0 | 1.0 |
| mg cholesterin ethoxylated with approx. 24 mols ethylene oxide $^{a)}$ | 25 | 25 | 25 | 25 | 25 | 25 |
| mg absolute ethanol | 300 | 300 | 300 | 300 | 300 | 300 |
| mg polyoxyethylene castor oil $^{h)}$ | 150 | 150 | 150 | 150 | 150 | — |
| mg ethoxylated oleic acid glyceride* | — | — | — | — | — | 200 |
| mg dibutylphthalate | — | 200 | — | — | — | — |
| mg isopropylmyristate | — | — | 150 | — | 150 | — |
| mg glycerinformal$^+$ | — | — | — | 150 | — | — |
| mg glycerinmonooleate$^{++}$ | — | — | to 1 ml | — | — | — |
| mg glycerinmonoacetate | — | — | — | — | to 1 ml | — |
| liquid triglyceride of saturated fatty acids of 8–12 carbon atoms $^{j)}$ | to 1 ml | to 1 ml | — | to 1 ml | — | to 1 ml |

*Labrafil M 1944 CS ®, Gattefosse SFPA
**Commercial product containing approx. 52% of monooleate and 30–50% dioleate. Th. Goldschmidt. Essen.
+As defined in Example 51

EXAMPLE 53:

Drop solutions of dihydroergotoxin

The formulations of Examples A to C, having the compositions indicated in the following table, are produced in manner analogous to those of Example 50.

| Component | Example | | |
|---|---|---|---|
| | A | B | C |
| mg dihydroergotoxin | 1.0 | 1.0 | 1.0 |
| mg sodium benzoic acid * sulphimide | 0.5 | 0.5 | 0.5 |
| mg polyethyleneglycol 400 | — | — | 300 |
| mg cholesterin ethoxylated with approx. 24 mols of ethylene oxide $^{a)}$ | 25 | 25 | 25 |
| mg glycerine | 300 | 300 | — |
| mg ethanol 94% w/w | 450 | 350 | to 0.1 ml |
| demineralised water | to 1 ml | to 1 ml | — |

*As defined in Example 51.

In one embodiment of the invention there is provided a liquid pharmaceutical composition comprising a clear micelle solution of one or more pharmaceutically active agents selected from the group consisting of ergot alkaloids, semisynthetic and synthetic lysergic acid derivatives in a liquid carrier composition containing from 0.5 to 10% by weight of a polyol etherified with cholesterin.

One suitable ergot alkaloid is ergotamine. Hydrogenated ergot alkaloids are especially preferred. Examples of hydrogenated ergot alkaloids which are particularly suitable are dihydroergotamine, dihydroergocristine, dihydroergotoxine, dihydroergocornine and dihydroergokryptine. Mixtures of these dihydroergot alkaloids can also be employed.

The pharmaceutically active agent may be employed in free base form or in the form of a pharmaceutically acceptable acid addition salts. Suitable acids for salt formation include methane sulphonic acid, acetic acid, maleic acid and tartaric acid.

In the case of a single dosage form, the pharmaceutically active agent or agents may, for example, amount to 1% by weight of the composition. With drop solutions, the active agent or agents may, for example, amount to from 0.05 to 5% by weight of the composition.

Suitable cholesterin derivatives are those which have been ethoxylated with from 15 to 25 mol of ethylene oxide, especially 24 mol.

The ratio of the quantity of the etherified polyol to the pharmaceutically active agent or agents may vary within broad limits and may, for example, be from 10 : 1 to 50 : 1, preferably from 20 : 1 to 30 : 1.

The components present in the compositions are conveniently present in such amounts that the quantity of the etherified polyol does not exceed 80 mg/unit dose, preferably not more than 50 mg/unit dose. Preferably, the final dosage form contains from 1 to 5%, especially from 2 to 3% by weight of the etherified polyol.

Suitable liquid components for the carrier composition include water and/or physiologically tolerable lower alcohols. The alcohols preferably contain 2 or 3 carbon atoms and may be straight chain or branched with one or more hydroxy groups. A particularly desirable alcohol is ethanol.

The quantity of the lower alcohol depends on the nature of the alcohol, the pharmaceutically active agent or agents employed and on other materials which may be present. The weight ratio of the alcohol to the etherified polyol may suitably be 5 or more, preferably from 7 to 10.

The type of liquid carrier material to be used depends on the pharmaceutically active material or materials employed, the polyol derivative and any other materials which may be present and on the desired form of the formulation. The liquid carrier material must be chosen to avoid incompatibility (such as causing precipitation or turbidity) with any of the aforementioned materials.

For the preparation of water-containing solutions, additional carrier materials may be used, for example, one or more water soluble, physiologically tolerable organic solvents such as one or more straight chain or branched lower alcohols, preferably containing from 2 to 6 carbon atoms, especially ethanol, glycerine, 2-methyl-2,4-pentadiol, cyclic etherified alcohol derivatives of polyfunctional alcohols, e.g. ketals or acetals such as formaldehyde acetals or acetone ketals or symmetrical and/or asymmetrical ethers. Examples of etherified alcohol derivatives include 4-hydroxymethyl-1,3-dioxolane, 5-hydroxy-1,3-dioxane, 4-hydroxymethyl-2,2-dimethyl-1,3-dioxolane or polyethylene glycol ethers of tetrahydrofurfuryl alcohol.

The same organic liquid carrier materials as described for the water-containing solutions may be employed in the preparation of the water-free solutions.

Oily liquid carriers, preferably neutral oils, may be employed in the preparation of water-free formulations. Such materials include liquid esters, preferably of saturated fatty acids, preferably those containing 8 to 12 carbon atoms, and lower polyfunctional alcohols, for example, oily triglyceride mixtures of saturated vegetable fatty acids of 8 to 12 carbon atoms, including isopropylmyristate, as well as phthalic acid esters, for example, dibutylphthalate. Soluble solid carrier materials which are physiologically tolerable and which are compatible with the other components of the formulation may also be employed. Such materials include esterified glycerine, for example, glycerine monooleate or monoacetate.

If desired, further materials may be added to the formulations, for example, preservatives, flavourings, flavour enhancers, buffer materials and emulsifiers. Water-containing solutions may suitably contain a physiologically tolerable buffer mixture which maintains the pH within a range of from 3.0 to 4.5, for example, a mixture of sodium acetate and acetic acid. Advantageously, a physiologically tolerable emulsifer can be added to the oily solutions, which makes it possible, before application, to dilute the solution with water to form an emulsion and which facilitates intake of the formulation and improves the taste thereof. Suitable emulsifiers include fatty acid esters of polyethylene glycol, for example, polyethylene glycol-400-stearate DAB7 (BRD) or fatty acid esters of polyethylene glycerine such as polyoxyethylene castor oil or ethoxylated oleic acid glyceride.

The compositions are preferably applied in oral form as drop solutions or syrups.

The preparation of the liquid compositions may be effected in known manner, wherein a pharmaceutically active agent or agents and etherified cholesterin are dissolved in the liquid carrier and, if desired, with the additional carrier materials or other additives.

The invention also provides a method of increasing the cumulative percentage absorption of pharmaceutically active agents administered enterally to an animal being treated with said agents, which comprises enterally administering in aggregates having a diameter of 20,000 A or less a therapeutically effective amount of said agents in combination with a pharmaceutically acceptable emulsifer having a mean HLB value of from 10 to 30, said emulsifer being present in said aggregate in an amount greater than 10 times the amount of said aggregate.

The method is particularly effective for active agents which are not readily absorbed into the bloodstream.

In another embodiment of the invention, there is provided a pharmaceutical composition for enteral administration comprising aggregates having a diameter of at most 20,000 A, which comprises:

a pharmaceutically active component a), containing at least one pharmaceutically acceptable active agent having a cumulative percentage absorption of 45 percent or less on enteral administration, and an emulsifer component b), containing at least one pharmaceutically acceptable emulsifier having a mean HLB value of 10 to 30, said component b) being present in said aggregates in an amount greater than 10 times by weight of component a).

Preferably the weight of the emulsifer having a mean HLB value of 10 to 30 to the pharmaceutically acceptable active agent or agents having a cumulative percentage absorption of 45% or less on enteral administration is greater than 10 : 1.

What is claimed is:

1. A pharmaceutical composition comprising aggregates of diameter of at most 20,000 A, comprising component a) a therapeutically effective amount of ergot alkaloid, and component b) a pharmaceutically acceptable ethoxylated cholesterin emulsifier having an HLB value of from 10 to 30 and present in an amount greater than 10 times by weight of the ergot alkaloid.

2. A pharmaceutical composition according to claim 1, wherein the ergot alkaloid is chosen from dihydroergotoxine, dihydroergocristine, 13-bromodihydroergocristine, dihydroergonine, dihydroergocryptine, dihydroergotamine, 13-bromodihydroergotamine, dihydroergocornine and dihydroergovaline, and ergotamine.

3. A pharmaceutical composition according to claim 1 wherein ergot alkalid is dihydroergonine, 4. A pharmaceutical composition according to claim 1, wherein the ratio of component b) to component a) is from 10 to 1 to 50 to 1.

5. A pharmaceutical composition according to claim 16, wherein the ratio of component b) to component a) is from 12 to 1 to 25 to 1.

6. A pharmaceutical composition according to claim 5, wherein the ratio of component b) to component a) is 25 to 1.

7. A pharmaceutical composition according to claim 1, wherein component b) is cholesterin ethoxylated with approximately 24 moles of ethylene oxide per mole cholesterin.

8. A method of increasing the enteral absorption of ergot alkaloids which comprises administering the alkaloid in a pharmaceutical composition comprising aggregates of diameter of at most 20,000 A, comprising component a) a therapeutically effective amount of ergot alkaloid, and component b) a pharmaceutically acceptable ethoxylated cholesterin emulsifer having an HLB value of from 10 to 30 and present in an amount greater than 10 times by weight of the ergot alkaloid.

9. A method according to claim 8, wherein the ergot alkaloid is chosen from dihydroergotoxine, dihydroergocristine, 13-bromodihydroergocristine, dihydroergonine, dihydroergocryptine, dihydroergotamine, 13-bromodihydroergotamine, dihydroergocornine and dihydroergovaline, and ergotamine.

10. A method according to claim 8, wherein ergot alkaloid is dihydroergonine.

11. A method according to claim 8, wherein the ratio of component b) to component a) is from 10 to 1 to 50 to 1.

12. A method according to claim 8, wherein the ratio of component b) to component a) is from 12 to 1 to 25 to 1.

13. A method according to claim 8, wherein the ratio of component b) to component a) is 25 to 1.

14. A method according to claim 8, wherein component b) is cholesterin ethoxylated with approximately 24 moles of ethylene oxide per mole cholesterin.

15. An ampoule containing a pharmaceutical composition according to claim 1.

16. A pharmaceutical composition according to claim 1, in the form of a capsule.

17. A pharmaceutical composition according to claim 1, in the form of a water-containing drop solution.

18. A pharmaceutical composition according to claim 1 in association with a pharmaceutically acceptable non-aqueous liquid carrier in the form of an anhydrous drop solution.

19. A pharmaceutical composition according to claim 1, in the form of a tablet.

* * * * *